(12) United States Patent
Horisaka et al.

(10) Patent No.: US 8,623,187 B2
(45) Date of Patent: Jan. 7, 2014

(54) GAS SENSOR

(75) Inventors: Sumiko Horisaka, Nagoya (JP); Hiroki Fujita, Kasugai (JP); Mika Murakami, Nagoya (JP); Takashi Ito, Kasugai (JP)

(73) Assignee: NGK Insulators, Ltd., Nagoya (JP)

( * ) Notice: Subject to any disclaimer, the term of this patent is extended or adjusted under 35 U.S.C. 154(b) by 0 days.

(21) Appl. No.: 13/053,605

(22) Filed: Mar. 22, 2011

(65) Prior Publication Data

US 2011/0233060 A1 Sep. 29, 2011

(30) Foreign Application Priority Data

Mar. 29, 2010 (JP) .................................. 2010-075186
Mar. 4, 2011 (JP) .................................. 2011-047517

(51) Int. Cl.
*G01N 27/417* (2006.01)
(52) U.S. Cl.
USPC ........... 204/424; 204/425; 204/426; 204/427; 204/428; 204/429; 73/23.31; 73/23.32
(58) Field of Classification Search
USPC ..................... 204/424–429; 73/23.31–23.32
See application file for complete search history.

(56) References Cited

U.S. PATENT DOCUMENTS

| | | | |
|---|---|---|---|
| 5,174,885 A * | 12/1992 | Hayakawa et al. | 204/425 |
| 6,224,727 B1 | 5/2001 | Miyata et al. | |
| 6,284,112 B1 | 9/2001 | Kato et al. | |
| 6,355,152 B1 | 3/2002 | Kato et al. | |
| 7,666,286 B2 | 2/2010 | Kurachi et al. | |
| 2004/0188251 A1* | 9/2004 | Kurachi et al. | 204/426 |
| 2005/0211554 A1* | 9/2005 | Kurachi et al. | 204/426 |
| 2008/0105545 A1* | 5/2008 | Nakagaki et al. | 204/424 |

FOREIGN PATENT DOCUMENTS

| | | |
|---|---|---|
| EP | 0 869 356 | 10/1998 |
| EP | 0 937 980 | 8/1999 |
| EP | 0 971 228 | 1/2000 |
| EP | 1 464 954 | 10/2004 |
| EP | 1 912 064 | 4/2008 |
| JP | 61-221644 | 10/1986 |
| JP | 61-296262 | 12/1986 |
| JP | 3176890 | 4/2001 |
| JP | 2004-317496 | 11/2004 |
| JP | 3701124 | 7/2005 |
| JP | 2009-236834 | 10/2009 |

OTHER PUBLICATIONS

Japanese Office Action, Japanese Application No. 2011-047517, dated Mar. 6, 2013 (6 pages).

* cited by examiner

*Primary Examiner* — Keith Hendricks
*Assistant Examiner* — Bach Dinh
(74) *Attorney, Agent, or Firm* — Burr & Brown, PLLC

(57) ABSTRACT

A gas sensor including a sensor element constituted by an oxygen-ion conductive solid electrolyte as a main component and detecting a predetermined gas component in a measurement gas includes: an external communication part having an opening opened to the outside, and introducing the measurement gas from the outside under a predetermined diffusion resistance; an internal space communicating with the external communication part; a first electrode formed on a surface of the internal space; a second electrode formed in a space different from the internal space; and a pumping cell operable to pump out oxygen existing in the internal space when a predetermined voltage is applied between the first electrode and the second electrode. The thickness of the external communication part is 50% or more and 100% or less of the thickness of the internal space.

5 Claims, 12 Drawing Sheets

F I G . 5
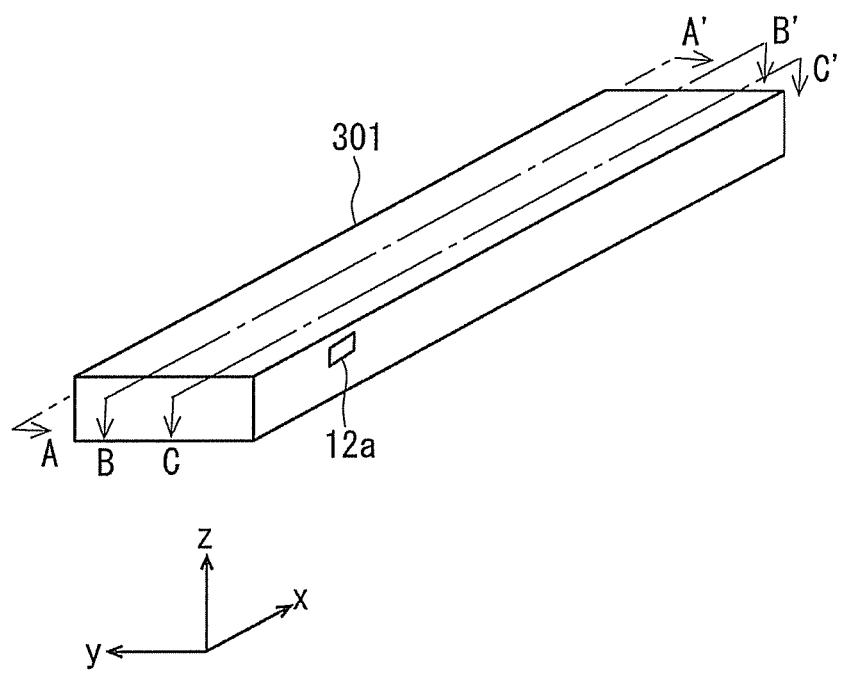

F I G . 7
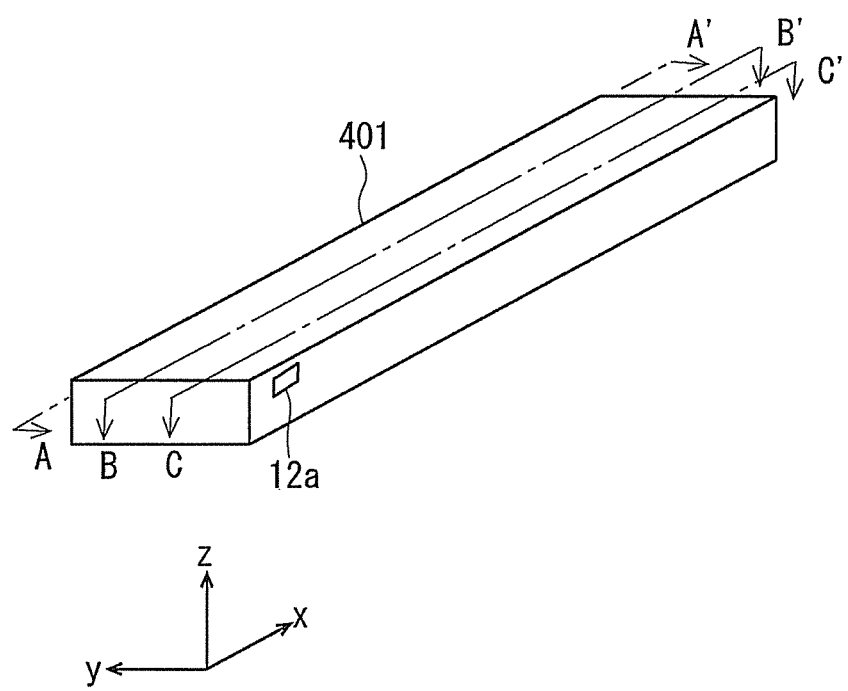

GAS SENSOR

BACKGROUND OF THE INVENTION

1. Field of the Invention

The present invention relates to a gas sensor including a sensor element and measuring a predetermined gas component in a measurement gas.

2. Description of the Background Art

Conventionally, various measuring apparatuses have been used for recognizing a concentration of a desired gas component in a measurement gas. For example, as a device for measuring a NOx concentration in a measurement gas such as a combustion gas, known is a gas sensor having an electrochemical pumping cell structured by forming a Pt electrode and a Rh electrode on an oxygen-ion conductive solid electrolyte layer, such as a zirconia ($ZrO_2$) layer. In this gas sensor, a diffusion control part communicating with the outside is formed so as to take a measurement gas from the outside into a sensor element and to apply a diffusion resistance suitable for measurement of a concentration of a desired gas component to the measurement gas.

For example, known is a gas sensor in which an opening communicating with the outside is provided in an end portion of a sensor element and a diffusion control part configured as a horizontally elongated slit is provided (for example, see Japanese Patent No. 3701124). Japanese Patent No. 3701124 discloses a gas sensor further including a gas inlet space before the slit-shaped diffusion control part mentioned above. Also known is a gas sensor including a diffusion control part formed by a porous body being filled in a portion of a sensor element for introducing a measurement gas from the outside so that a diffusion resistance suitable for measurement of a concentration of a desired gas component can be applied to the measurement gas during take-in of the measurement gas into the sensor element from the outside (for example, see Japanese Patent No. 3176890).

The gas sensors disclosed in Japanese Patent No. 3701124 and Japanese Patent No. 3176890 are, for example, installed in an exhaust pipe of an internal combustion engine such as an automobile engine, and used to measure a concentration of a desired gas component contained in an exhaust gas. In such an internal combustion engine, in a case where driving thereof is stopped, water vapor contained in the exhaust gas may be condensed to form a water droplet. Such a water droplet is not only accumulated in the exhaust pipe but also adheres to the gas sensor.

Generally, a gas sensor is mounted in an exhaust pipe so as to be substantially perpendicularly to a flow of an exhaust gas while a protective covering having a gas inlet hole through which a gas can freely pass is provided at the outer side of a sensor element. Therefore, in a case where a water droplet adheres to the inside of the protective covering, a part of the water droplet is discharged through the gas inlet hole. However, the water droplet still stays at a bottom portion of the protective covering. Since the bottom portion of the protective covering is in close contact with an end portion of the sensor element, when an internal combustion engine is re-driven, a considerable part of the water droplet staying at the bottom portion of the protective covering adheres to the end portion of the sensor element. Additionally, a water droplet staying within the exhaust pipe may splash within the protective covering to adhere to the end portion of the sensor element.

As a result, the adhering of the water droplet partially cools only the end portion, to cause a temperature gradient between the end portion and the inside of the sensor element. Moreover, a thermal stress resulting from this temperature gradient may cause cracking.

Additionally, water adhering to the end portion of the sensor element may reach an internal space through a slit-shaped diffusion control part formed in the end portion of the sensor element due to the capillarity. In a case where the internal combustion engine is driven in this state, the water rapidly vaporizes in the internal space to cause cracking in the sensor element.

In this manner, occurrence of cracking in the sensor element largely changes a diffusion resistance to be applied to the measurement gas, which is not preferable because a measurement accuracy is deteriorated.

SUMMARY OF THE INVENTION

The present invention is directed to a gas sensor for measuring a predetermined gas component in a measurement gas, and particularly relates to a structure of a sensor element forming the gas sensor.

According to the present invention, a gas sensor detecting a predetermined gas component in a measurement gas includes a sensor element constituted by an oxygen-ion conductive solid electrolyte as a main component. The said sensor element includes: an external communication part having an opening opened to the outside, and introducing the measurement gas from the outside under a predetermined diffusion resistance; an internal space communicating with the external communication part; a first electrode formed on a surface of the internal space; a second electrode formed in a space different from the internal space; and a pumping cell operable to pump out oxygen existing in the internal space when a predetermined voltage is applied between the first electrode and the second electrode. The thickness of the external communication part is 50% or more and 100% or less of the thickness of the internal space.

This can achieve a gas sensor whose measurement accuracy is stably maintained even if water adheres to an end portion of the sensor element.

Preferably, the sensor element included in the gas sensor according to the present invention further includes a buffer space provided between the external communication part and the internal space.

This can achieve a gas sensor in which a concentration fluctuation in the measurement gas can be suitably suppressed even if the measurement gas is abruptly taken into the sensor element along with a pressure fluctuation in the measurement gas existing in the outside.

Preferably, in the gas sensor according to the present invention, the external communication part has the opening formed in a side portion or an end portion of the sensor element.

This can achieve a gas sensor which can suppress entry of water adhering to the end portion of the sensor element into the sensor element due to the capillarity.

Therefore, an object of the present invention is to provide a gas sensor whose measurement accuracy can be stably maintained.

BRIEF DESCRIPTION OF THE DRAWINGS

FIG. 5 is a perspective view showing an outline of an exemplary configuration of a sensor element of a gas sensor according to a third preferred embodiment;

FIG. 7 is a perspective view showing an outline of an exemplary configuration of a sensor element of a gas sensor according to a fourth preferred embodiment;

DETAILED DESCRIPTION OF THE INVENTION

First Preferred Embodiment

<Outline Configuration of Gas Sensor>

Firstly, an outline configuration of a gas sensor 100 will be described.

Figure 1:
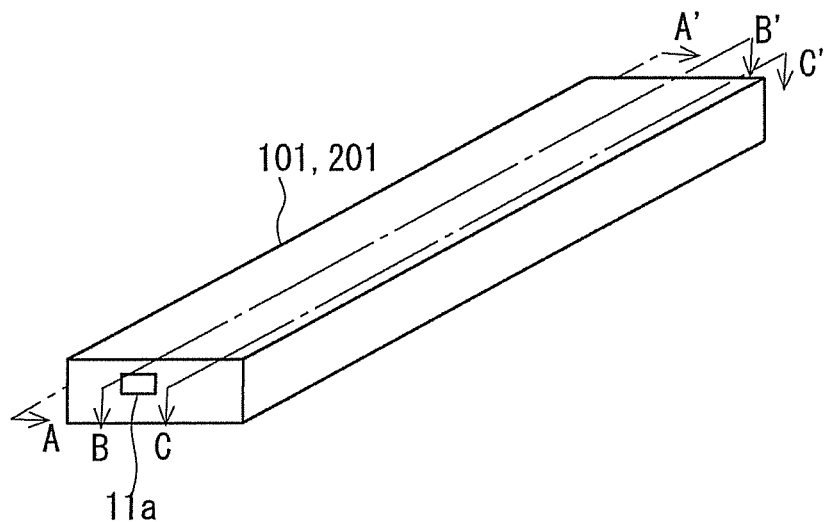
FIG. 1 is a perspective view showing an outline of an exemplary configuration of a sensor element of a gas sensor according to a first preferred embodiment.
Figure 2A:
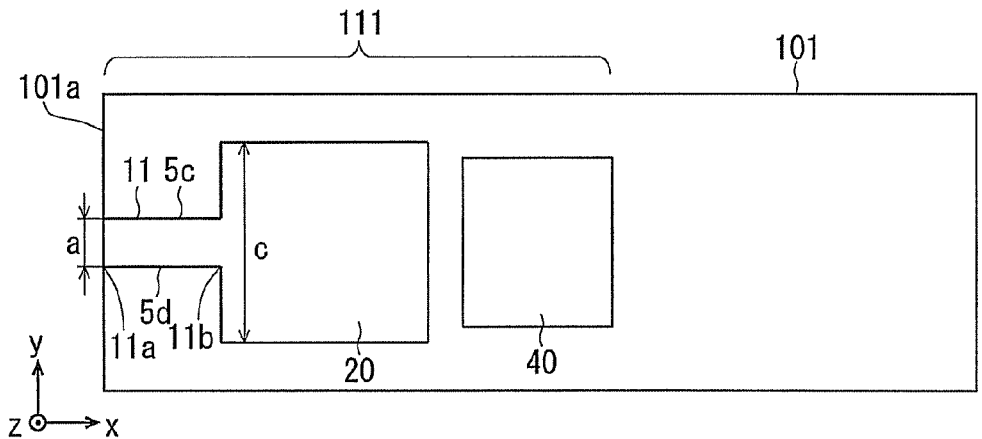
FIGS. 2A, 2B, and 2C are schematic cross-sectional views showing outline cross-sections of the sensor element of the gas sensor according to the first preferred embodiment.
Figure 2B:
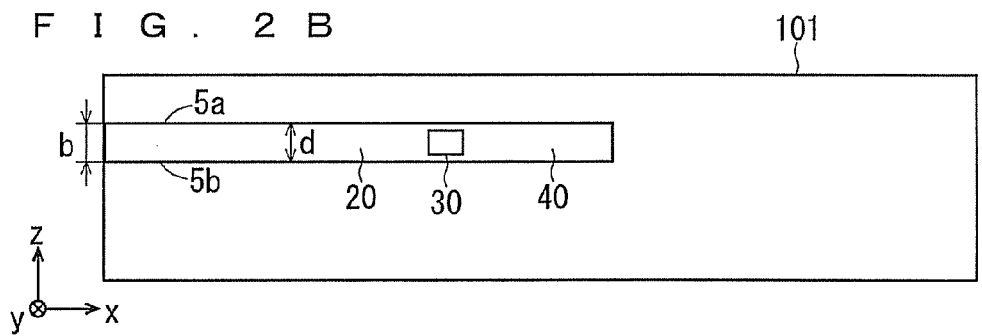
Figure 2C:
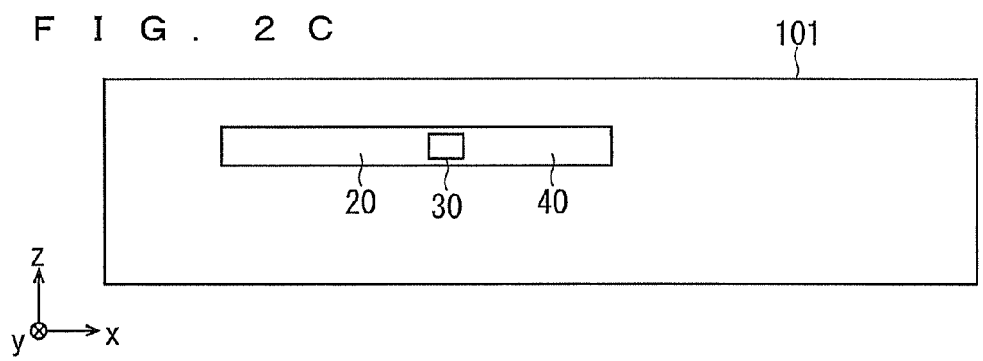
Figure 3:
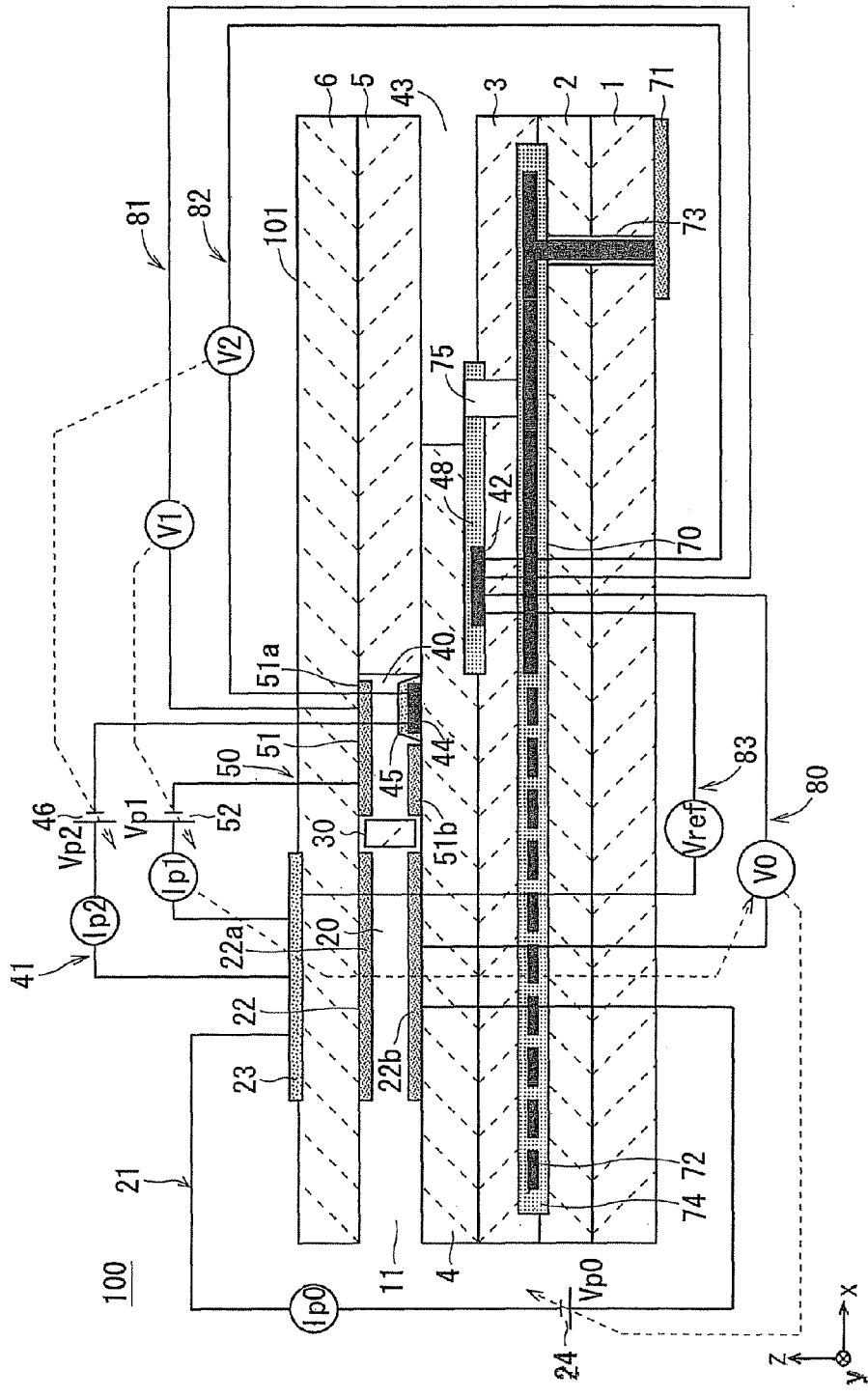
FIG. 3 is a schematic cross-sectional view showing an exemplary configuration of the gas sensor according to the first preferred embodiment.

FIG. 1 is an external appearance perspective view showing an outline of an exemplary configuration of a sensor element 101 of the gas sensor 100. FIG. 1 shows a right-hand xyz coordinate system in which the longitudinal direction of the sensor element 101 is defined as the x-axis (hereinafter, the same is true). FIGS. 2A, 2B, and 2C are schematic cross-sectional views showing outline cross-sections of the sensor element 101 as sectioned at different positions shown in FIG. 1, for explaining the structure of a gas distribution part 111. In FIGS. 2A, 2B, and 2C, for simplification, components other than the gas distribution part 111 are omitted. FIG. 2A shows a cross-section as sectioned along the arrow A-A' of FIG. 1. FIG. 2B shows a cross-section as sectioned along the arrow B-B' of FIG. 1. FIG. 2C shows a cross-section as sectioned along the arrow C-C' of FIG. 1. FIG. 3 is a schematic cross-sectional view showing an example of a detailed configuration of the gas sensor 100.

The sensor element 101 is an elongated plate-shaped element having a structure in which six layers, namely, a first substrate layer 1, a second substrate layer 2, a third substrate layer 3, a first solid electrolyte layer 4, a spacer layer 5, and a second solid electrolyte layer 6, are laminated in the mentioned order from the bottom side seen in FIG. 3, each of the layers being formed as an oxygen-ion conductive solid electrolyte layer such as a zirconia ($ZrO_2$) layer. The solid electrolyte forming these six layers is densely airtight. The sensor element 101 is manufactured by, for example, performing a predetermined process and printing a circuit pattern on ceramic green sheets, each of which corresponds to each of the layers, then laminating the green sheets, then cut the laminated body into element units, and furthermore baking the laminated body to integrate it.

Between a lower surface of the second solid electrolyte layer 6 and an upper surface of the first solid electrolyte layer 4 at one end portion of the sensor element 101, an external communication part 11, a first internal space 20, a first diffusion control part 30, and a second internal space 40 are adjacently formed in the mentioned order so as to be in communication with one another.

The external communication part 11 is a space within the sensor element 101 provided by hollowing out the spacer layer 5, in which its upper portion is defined by the lower surface of the second solid electrolyte layer 6 or an internal surface 5a of the spacer layer 5, its lower portion is defined by the upper surface of the first solid electrolyte layer 4 or an internal surface 5b of the spacer layer 5, and its side portion is defined by side surfaces 5c and 5d of the spacer layer 5. In more detail, the position where the external communication part 11 is formed is adjusted in accordance with the degree of a diffusion resistance suitable for measurement of a nitrogen oxide (NOx) concentration, which will be described later.

The first internal space 20 and the second internal space 40 are also spaces within the sensor element 101 provided by hollowing out the spacer layer 5, in which their upper portions are defined by the lower surface of the second solid electrolyte layer 6, their lower portions are defined by the upper surface of the first solid electrolyte layer 4, and their side portions are defined by the side surfaces of the spacer layer 5.

The first diffusion control part 30 is configured as two horizontally long slits (whose openings are elongated in a y-axis direction). A part extending from the external communication part 11 to the second internal space 40 is also referred to as a gas distribution part 111.

In the other end portion of the sensor element 101, at a position which is farther from an end portion 101a of the element than the gas distribution part 111 is, a reference gas inlet space 43 is provided between an upper surface of the third substrate layer 3 and a lower surface of the spacer layer 5. A side portion of the reference gas inlet space 43 is defined by a side surface of the first solid electrolyte layer 4. As a reference gas for measuring a NOx concentration, for example, air is introduced into the reference gas inlet space 43.

An air introduction layer 48 is constituted by porous alumina. The reference gas is introduced through the reference gas inlet space 43 into the air introduction layer 48. The air introduction layer 48 is fowled so as to cover a reference electrode 42.

The reference electrode 42 is an electrode formed so as to be interposed between the upper surface of the third substrate layer 3 and the first solid electrolyte layer 4. As described above, the air introduction layer 48 leading to the reference gas inlet space 43 is provided around the reference electrode 42. By using the reference electrode 42, an oxygen concentration (oxygen partial pressure) in the internal space can be measured, as will be described later.

<Details of Gas Distribution Part and Associated Parts>

The external communication part 11 applies a predetermined diffusion resistance suitable for measurement of a nitrogen oxide (NOx) concentration to the measurement gas introduced through an opening 11a formed in the end portion 101a of the sensor element from the outside, and then guides the resistant measurement gas to the first internal space 20 communicating with the external communication part 11 through a communication part 11b.

A width a of the external communication part 11 in the y-axis direction and a thickness b thereof in a z-axis direction are defined in accordance with the degree of the diffusion resistance to be applied to the measurement gas introduced from the opening 11a into the first internal space 20.

Here, it is preferable that the thickness b of the external communication part 11 is 50% to 100% of a thickness (hollow-chamber thickness) d of the first internal space 20 in the z-axis direction, and the width a of the external communication part 11 is 5% to 60% (desirably 10% to 40%) of a width (hollow-chamber width) c of the first internal space 20 in the y-axis direction.

The thickness b less than 50% of the thickness d is not preferable, because the opening 11a has a reduced opening area so that water adhering to the end portion 101a of the sensor element may easily enter the first internal space 20 due to the capillarity. The width a less than 5% of the width c is not preferable, because the opening 11a has a reduced opening area so that water adhering to the end portion 101a of the sensor element may easily enter the first internal space 20 due to the capillarity. The width a more than 60% of the width c makes it difficult that a diffusion resistance suitable for measurement of the nitrogen oxide (NOx) concentration is applied to the measurement gas.

In this manner, in the gas sensor 100, the width a and the thickness b of the external communication part 11 are defined within the range mentioned above, thereby suppressing entry of water adhering to the end portion 101a of the sensor element into the first internal space 20.

The first internal space 20 is provided as a space for adjusting the oxygen partial pressure in the measurement gas introduced through the external communication part 11. This oxygen partial pressure is adjusted by an operation of a main pumping cell 21.

The main pumping cell 21 is an electrochemical pumping cell constituted by an inside pump electrode 22, an outside pump electrode 23, and a part of the second solid electrolyte layer 6 interposed between these electrodes. The inside pump electrode 22 has a ceiling electrode portion 22a provided on a substantially entire part of the lower surface of the second solid electrolyte layer 6 facing the first internal space 20. The outside pump electrode 23 is provided in a region on an upper surface of the second solid electrolyte layer 6 corresponding to the ceiling electrode portion 22a, so as to be exposed to the outside.

The inside pump electrode 22 is formed over the upper and lower solid electrolyte layers (the second solid electrolyte layer 6 and the first solid electrolyte layer 4) which define the first internal space 20, and the spacer layer 5 which provides a side wall to the first internal space 20. To be specific, the ceiling electrode portion 22a is formed on the lower surface of the second solid electrolyte layer 6 which provides a ceiling surface to the first internal space 20. A bottom electrode portion 22b is formed on the upper surface of the first solid electrolyte layer 4 which provides a bottom surface to the first internal space 20. A side electrode portion (not shown) connecting the ceiling electrode portion 22a to the bottom electrode portion 22b is formed on side wall surfaces (inner surfaces) of the spacer layer 5 which form both side wall portions of the first internal space 20. Thus, the inside pump electrode 22 has a tunnel-like shape at a location where the side electrode portion is disposed.

Each of the inside pump electrode 22 and the outside pump electrode 23 is formed as a porous cermet electrode (for example, a cermet electrode including Pt containing Au by 1% and zirconia). The inside pump electrode 22 which is brought into contact with the measurement gas is formed using a material having a weakened reduction ability with respect to a NOx component in the measurement gas, or having no reduction ability with respect to the NOx component in the measurement gas.

In the main pumping cell 21, a desired pump voltage $Vp0$ is applied between the inside pump electrode 22 and the outside pump electrode 23 to make a pump current $Ip0$ flow in a positive direction or a negative direction between the inside pump electrode 22 and the outside pump electrode 23, and this allows oxygen existing within the first internal space 20 to be pumped out to the outside or oxygen existing in the outside to be pumped into the first internal space 20.

In order to detect an oxygen concentration (oxygen partial pressure) in the atmosphere of the first internal space 20, an electrochemical sensor cell, in other words, a main-pump-controlling oxygen-partial-pressure detection sensor cell 80 is formed with the inside pump electrode 22, the second solid electrolyte 6, the spacer layer 5, the first solid electrolyte 4, the third substrate layer 3, and the reference electrode 42.

The oxygen concentration (oxygen partial pressure) in the first internal space 20 can be recognized by measuring an electromotive force $V0$ of the main-pump-controlling oxygen-partial-pressure detection sensor cell 80. Moreover, the pump current $Ip0$ is controlled by feedback-controlling $Vp0$ so as to maintain the electromotive force $V0$ constant. Thereby, the oxygen concentration in the first internal space 20 can be maintained at a predetermined constant value.

The first diffusion control part 30 applies a predetermined diffusion resistance to the measurement gas whose oxygen concentration (oxygen partial pressure) has been controlled in the first internal space 20 by the operation of the main pumping cell 21, and guides the measurement gas to the second internal space 40.

The second internal space 40 is provided as a space for performing a process concerning measurement of the nitrogen oxide (NOx) concentration in the measurement gas introduced through the first diffusion control part 30. In the second internal space 40 in which the oxygen concentration in the measurement gas is adjusted by an auxiliary pumping cell 50, the NOx concentration is measured by the operation of a measuring pumping cell 41.

In the second internal space 40, the auxiliary pumping cell 50 performs further adjustment of oxygen partial pressure on the measurement gas whose oxygen concentration (oxygen partial pressure) has been adjusted in advance in the first internal space 20 and which has then been introduced through the first diffusion control part 30. This enables an oxygen concentration in the second internal space 40 to be accurately maintained constant. Therefore, the gas sensor 100 can measure a NOx concentration with a high accuracy.

The auxiliary pumping cell 50 is an auxiliary electrochemical pumping cell constituted by an auxiliary pump electrode 51, the outside pump electrode 23 (not limited to the outside pump electrode 23 but may be any appropriate electrode positioned outside the sensor element 101), and the second solid electrolyte layer 6. The auxiliary pump electrode 51 has a ceiling electrode portion 51a provided on a substantially entire part of the lower surface of the second solid electrolyte layer 6 facing the second internal space 40.

Similarly to the inside pump electrode 22 provided in the first internal space 20, the auxiliary pump electrode 51 has a tunnel-like shape and provided in the second internal space 40. That is, the ceiling electrode portion 51a is formed on the second solid electrolyte layer 6 which provides a ceiling surface to the second internal space 40. A bottom electrode portion 51b is formed on the first solid electrolyte layer 4 which provides a bottom surface to the second internal space 40. A side electrode portion (not shown) connecting the ceiling electrode portion 51a to the bottom electrode portion 51b is formed on both wall surfaces of the spacer layer 5 which provides side walls to the second internal space 40.

Similarly to the inside pump electrode 22, the auxiliary pump electrode 51 is unwed using a material having a weakened reduction ability with respect to a NOx component in the measurement gas, or having no reduction ability with respect to the NOx component in the measurement gas.

In the auxiliary pumping cell 50, a desired voltage Vp1 is applied between the auxiliary pump electrode 51 and the outside pump electrode 23, and this allows oxygen existing in the atmosphere of the second internal space 40 to be pumped out to the outside or oxygen existing in the outside to be pumped into the second internal space 40.

In order to control oxygen partial pressure in the atmosphere of the second internal space 40, an electrochemical sensor cell, in other words, an auxiliary-pump-controlling oxygen-partial-pressure detection sensor cell 81 is formed with the auxiliary pump electrode 51, the reference electrode 42, the second solid electrolyte layer 6, the spacer layer 5, the first solid electrolyte layer 4, and the third substrate layer 3.

A variable power source 52 causes the auxiliary pumping cell 50 to perform pumping. The variable power source 52 is voltage-controlled based on an electromotive force V1 which is detected by the auxiliary-pump-controlling oxygen-partial-pressure detection sensor cell 81. Therefore, the oxygen partial pressure in the atmosphere of the second internal space 40 is lowered to have substantially no influence on the NOx measurement.

At the same time, a pump current Ip1 of the auxiliary pumping cell 50 is used for a control of the electromotive force of the main-pump-controlling oxygen-partial-pressure detection sensor cell 80. Specifically, the pump current Ip1 is inputted as a control signal to the main-pump-controlling oxygen-partial-pressure detection sensor cell 80, and its electromotive force V0 is controlled, so that a gradient of the oxygen partial pressure in the measurement gas introduced into the second internal space 40 through the first diffusion control part 30 is maintained so as to be always constant. When used as a NOx sensor, the oxygen concentration in the second internal space 40 is maintained at a constant value of approximately 0.001 ppm, by the operations of the main pumping cell 21 and the auxiliary pumping cell 50.

Thus, in the gas sensor 100, by operating the main pumping cell 21 and the auxiliary pumping cell 50, the oxygen partial pressure is always maintained to be a constant low value (value having substantially no influence on the measurement of NOx).

The measurement gas whose oxygen concentration has been adjusted in the second internal space 40 is measured for the NOx concentration by the operation of the measuring pumping cell 41. The measuring pumping cell 41 is an electrochemical pumping cell constituted by a measuring electrode 44, the outside pump electrode 23, the second solid electrolyte layer 6, the spacer layer 5, and the first solid electrolyte layer 4. The measuring electrode 44 is provided at a position on the upper surface of the first solid electrolyte layer 4 facing the second internal space 40.

The measuring electrode 44 is a porous cermet electrode. The measuring electrode 44 also functions as a NOx reducing catalyst which reduces NOx existing in the atmosphere of the second internal space 40. The measuring electrode 44 is covered with a second diffusion control part 45.

The second diffusion control part 45 is a film constituted by a porous body containing alumina ($Al_2O_3$) as a main component. The second diffusion control part 45 serves to limit the amount of NOx flowing into the measuring electrode 44, and also functions as a protective film of the measuring electrode 44.

The measuring pumping cell 41 can pump out oxygen generated by decomposition of nitrogen oxide in the atmosphere around the measuring electrode 44, and detects the amount of the generated oxygen as a pump current Ip2.

In order to detect oxygen partial pressure around the measuring electrode 44, an electrochemical sensor cell, in other words, a measuring-pump-controlling oxygen-partial-pressure detection sensor cell 82 is formed with the second solid electrolyte layer 6, the spacer layer 5, the first solid electrolyte layer 4, the third substrate layer 3, the measuring electrode 44, and the reference electrode 42. A variable power source 46 is controlled based on an electromotive force V2 detected by the measuring-pump-controlling oxygen-partial-pressure detection sensor cell 82.

As described above, the measurement gas introduced into the second internal space 40 reaches the measuring electrode 44 through the second diffusion control part 45 while the oxygen partial pressure in the measurement gas is being controlled. Nitrogen oxide in the measurement gas existing around the measuring electrode 44 is reduced ($2NO \rightarrow N_2 + O_2$), to generate oxygen. The generated oxygen is pumped by the measuring pumping cell 41. At this time, a voltage Vp2 of the variable power source is controlled such that a control voltage V2 detected by the measuring-pump-controlling oxygen-partial-pressure detection sensor cell 82 can be maintained constant. The amount of oxygen generated around the measuring electrode 44 is proportional to a nitrogen-oxide concentration in the measurement gas. Thus, the nitrogen-oxide concentration in the measurement gas is calculated by using the pump current Ip2 of the measuring pumping cell 41.

In other words, in the gas sensor 100, the NOx concentration in the measurement gas can be recognized based on the pump current Ip2 which flows when the oxygen generated by the reduction of NOx is pumped out by the measuring pumping cell 41 substantially in proportion to the NOx concentration in the measurement gas.

An electrochemical sensor cell 83 is formed with the second solid electrolyte layer 6, the spacer layer 5, the first solid electrolyte layer 4, the third substrate layer 3, the outside pump electrode 23, and the reference electrode 42. By an electromotive force Vref obtained by the sensor cell 83, oxygen partial pressure in the measurement gas existing in the outside of the sensor can be detected.

<Heater Part>

Furthermore, in order to enhance an oxygen-ion conductivity of the solid electrolyte, the sensor element 101 includes a heater part 70 serving for a temperature control for heating and keeping warm the sensor element 101. The heater part 70 includes a heater electrode 71, a heater 72, a through hole 73, a heater insulating layer 74, and a pressure diffusion hole 75

The heater electrode 71 is an electrode formed in contact with a lower surface of the first substrate layer 1. By connecting the heater electrode 71 to an external power source, electrical power can be supplied to the heater part 70 from the outside.

The heater 72 is an electric resistor interposed vertically between the second substrate layer 2 and the third substrate layer 3. The heater 72 is connected to the heater electrode 71 via the through hole 73. The heater 72 generates heat when power is supplied from the outside through the heater electrode 71, and heats and keeps warm the solid electrolyte which forms the sensor element 101.

The heater 72 is buried over the entire area extending from the first internal space 20 to the second internal space 40, so that the temperature of the entire sensor element 101 can be adjusted at a temperature at which the solid electrolyte is activated.

The heater insulating layer 74 is an insulating layer constituted by an insulator such as alumina and formed on upper and lower surfaces of the heater 72. The heater insulating layer 74 is formed for the purpose of providing an electrical insulation between the second substrate layer 2 and the heater 72 and an electrical insulation between the third substrate layer 3 and the heater 72.

The pressure diffusion hole 75 is formed through the third substrate layer 3, and communicates with the reference gas inlet space 43. The pressure diffusion hole 75 is formed for the purpose of relieving a rise in the internal pressure which is involved in a temperature rise in the heater insulating layer 74.

As described above, in the gas sensor 100 according to this preferred embodiment, the size of the external communication part 11 having the opening 11a formed in the end portion 101a of the sensor element 101 is suitably set, thereby suppressing entry of water adhering to the end portion 101a of the sensor element into the internal space due to the capillarity. This can consequently suppress occurrence of cracking in the sensor element 101 which may otherwise be caused by rapid vaporization of the water in the internal space.

Therefore, in the gas sensor 100 according to this preferred embodiment, a deterioration in the measurement accuracy which may be caused by occurrence of cracking in the sensor element 101 can be suitably suppressed. In other words, even if water adheres to the end portion 101a of the sensor element 101 during the operation of the gas sensor 100, the measurement accuracy is stably maintained.

In a case where the thickness b of the external communication part 11 is made equal to the thickness d of the first internal space 20, the sensor element 101 can be formed by, in the above-mentioned green-sheet process, forming an opening serving as the external communication part 11 simultaneously with forming openings serving as the first internal space 20 and the second internal space 40 in the ceramic green sheet serving as the spacer layer 5 by punching, and then performing the same process steps as described above.

In a case where the thickness b of the external communication part 11 is made smaller than the thickness d of the first internal space 20, a green sheet which will be laminated between the first solid electrolyte layer 4 and the spacer layer 5 or between the spacer layer 5 and the second solid electrolyte layer 6 may be separately prepared in addition to the green sheets serving as the six layers, then a cutout may be formed in the ceramic green sheet by punching in the above-mentioned green-sheet process, then the green sheets including this green sheet may be laminated, and then the same process steps as described above may be performed.

Alternatively, in the above-mentioned green-sheet process, a paste with sublimation properties to form the external communication part 11 may be printed on the first solid electrolyte layer 4 or the spacer layer 5, when printing a predetermined circuit pattern on the ceramic green sheets serving as the respective layers. In this case, the paste is sublimed at a time of baking, to form the external communication part 11.

As described above, according to this preferred embodiment, the external communication part 11 having a predetermined size is provided in the end portion 101a of the sensor element 101, to thereby achieve a gas sensor whose measurement accuracy is stably maintained even if water adheres to the end portion 101a of the sensor element 101 during the operation.

Second Preferred Embodiment

In a second preferred embodiment, a configuration in which a gas distribution part is different from that of the gas sensor 100 according to the first preferred embodiment will be described.

An external appearance perspective view showing an exemplary configuration of a sensor element 201 of a gas sensor 200 according to the second preferred embodiment is identical to that of the gas sensor 100 according to the first preferred embodiment. Therefore, here, FIG. 1 is referred to.

Figure 4A:
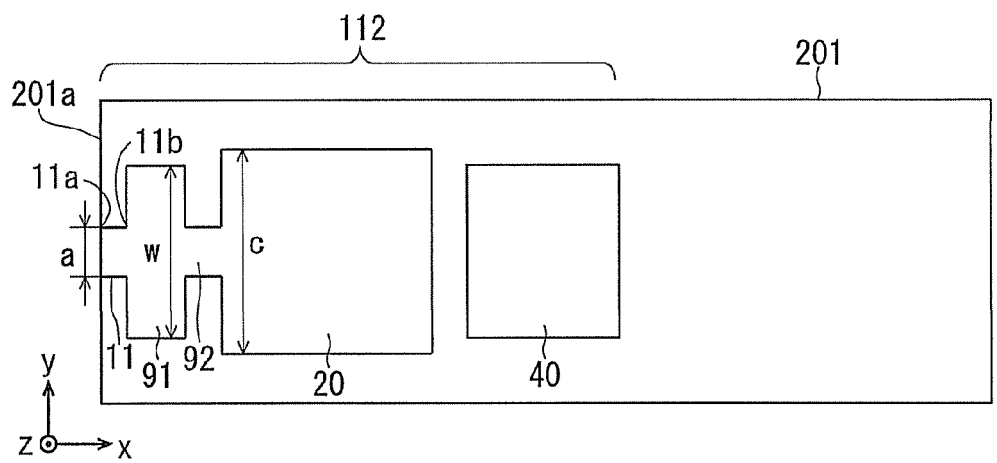
FIGS. 4A, 4B, and 4C are schematic cross-sectional views showing outline cross-sections of a sensor element of a gas sensor according to a second preferred embodiment.
Figure 4B:
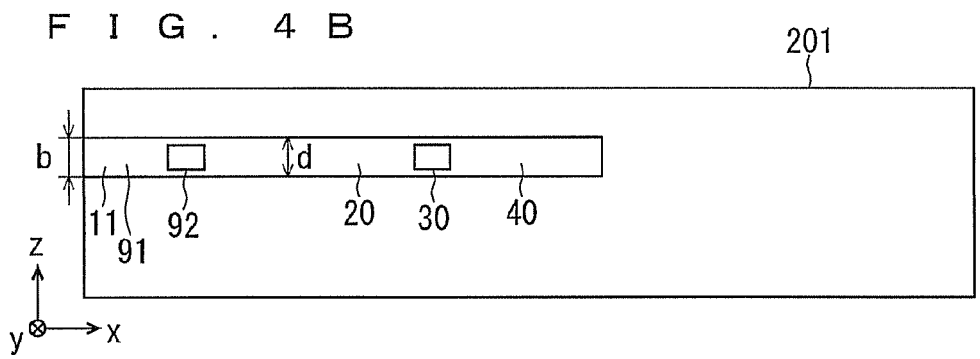
Figure 4C:
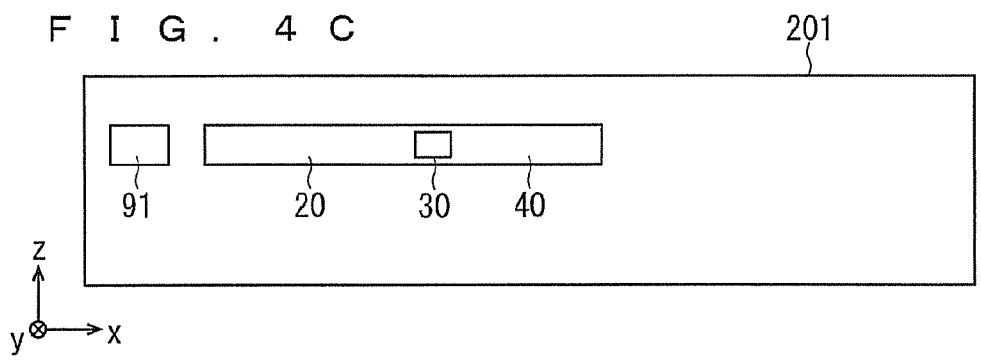

FIGS. 4A, 4B, and 4C are schematic cross-sectional views showing outline cross-sections of the sensor element 201 sectioned at different positions shown in FIG. 1, for explaining the structure of a gas distribution part 112. In FIGS. 4A, 4B, and 4C, for simplification, components other than the gas distribution part 112 are omitted. FIG. 4A shows a cross-section as sectioned along the arrow A-A' of FIG. 1. FIG. 4B shows a cross-section as sectioned along the arrow B-B' of FIG. 1. FIG. 4C shows a cross-section as sectioned along the arrow C-C' of FIG. 1. The same components as those of the gas sensor 100 according to the first preferred embodiment are denoted by the same corresponding reference numerals, and descriptions and drawings thereof are omitted.

In the sensor element 201, a buffer space 91 and a third diffusion control part 92 are provided between the external communication part 11 and the first internal space 20 of the sensor element 101 according to the first preferred embodiment. In this preferred embodiment, a part extending from the external communication part 11 to the second internal space 40 is also referred to as a gas distribution part 112.

Similarly to the external communication part 11, the buffer space 91 is a space within the sensor element 101 provided by hollowing out the spacer layer 5, in which its upper portion is defined by the lower surface of the second solid electrolyte layer 6, its lower portion is defined by the upper surface of the first solid electrolyte layer 4, and its side portions are defined by the side surface of the spacer layer 5. Here, the buffer space 91 is formed such that its width w in the y-axis direction can be larger than the width a of the external communication part 11.

Providing the buffer space 91 can reduce an influence of a pressure fluctuation of the measurement gas existing in the outside (a pulsation of exhaust gas pressure, in a case where the measurement gas is an automobile exhaust gas) while the measurement gas is being introduced from the outside of the sensor element 201 into the first internal space 20 of the sensor element 201. Thus, even if the measurement gas is abruptly taken due to the pressure fluctuation, a concentration fluctuation in the measurement gas introduced into the first internal space 20 is substantially negligible.

The third diffusion control part 92 applies a predetermined diffusion resistance to the measurement gas introduced from the buffer space 91 to the first internal space 20. The third diffusion control part 92 is configured as two horizontally long slits (whose openings are elongated in the y-axis direction).

In the sensor element 201, the external communication part 11, the buffer space 91, and the third diffusion control part 92, as a whole, apply a predetermined diffusion resistance suitable for measurement of the nitrogen oxide (NOx) concentration to the measurement gas introduced from the opening 11a to the second internal space 20.

The values of the width a and the thickness b which define the value of the diffusion resistance applied in the external communication part 11 may be set in consideration of the relationship with the diffusion resistance to be applied in the third diffusion control part 92. In this preferred embodiment, similarly to the first preferred embodiment, it is preferable that the thickness b of the external communication part 11 is 50% to 100% of the thickness d of the first internal space 20 in the z-axis direction, and the width a of the external communication part 11 is 5% to 60% (desirably 10% to 40%) of the width c of the first internal space 20 in the y-axis direction. This can suppress occurrence of the capillarity.

As described above, according to this preferred embodiment, similarly to the first preferred embodiment, even if water adheres to the end portion 101a of the sensor element 101 during the operation, the measurement accuracy is stably maintained. Moreover, since the buffer space 91 and the third diffusion control part 92 are provided, a gas sensor can be achieved in which a concentration fluctuation in the measurement gas is suppressed even if the measurement gas is abruptly taken into the sensor element 201 along with a pressure fluctuation of the measurement gas existing in the outside.

Third Preferred Embodiment

In a third preferred embodiment, the position where an external communication part is provided is different from that of the gas sensor 100 according to the first preferred embodiment.

Figure 6A:
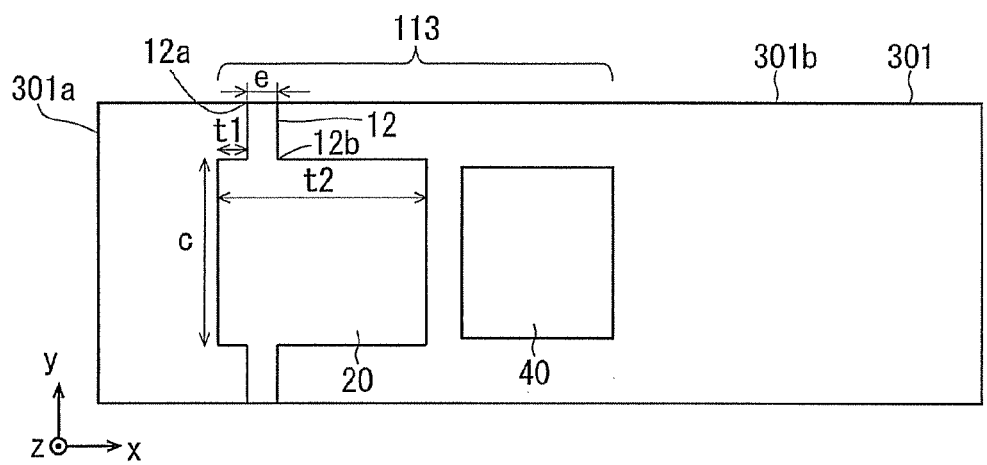
FIGS. 6A, 6B, and 6C are schematic cross-sectional views showing outline cross-sections of the sensor element of the gas sensor according to the third preferred embodiment.
Figure 6B:
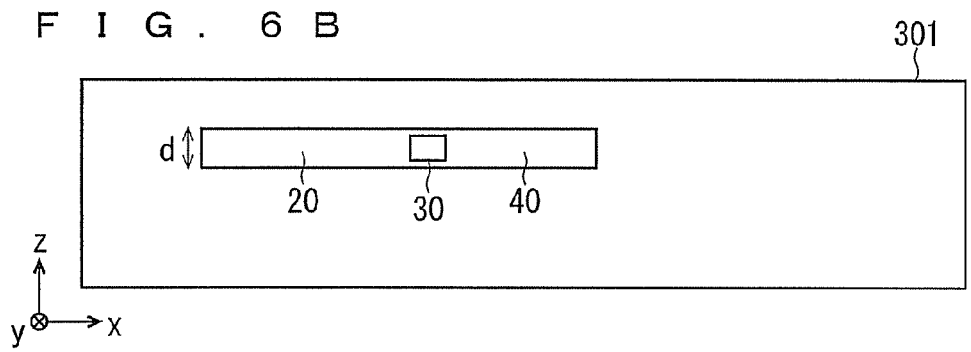
Figure 6C:
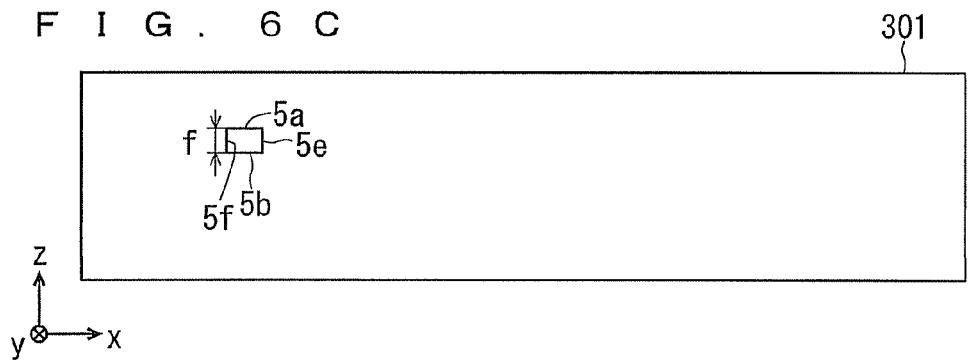

FIG. 5 is an external appearance perspective view showing an outline of an exemplary configuration of a sensor element 301 of a gas sensor 300 according to the third preferred embodiment. FIGS. 6A, B, and 6C are schematic cross-sectional views showing outline cross-sections of the sensor element 301 as sectioned at different positions shown in FIG. 5, for explaining the structure of a gas distribution part 113. In FIGS. 6A, B, and 6C, for simplification, components other than the gas distribution part 113 are omitted. FIG. 6A shows a cross-section as sectioned along the arrow A-A' of FIG. 5. FIG. 6B shows a cross-section as sectioned along the arrow B-B' of FIG. 5. FIG. 6C shows a cross-section as sectioned along the arrow C-C' of FIG. 5. The same components as those of the gas sensor 100 according to the first preferred embodiment and the gas sensor 200 according to the second preferred embodiment are denoted by the same corresponding reference numerals, and descriptions and drawings thereof are omitted.

In the sensor element 301, external communication parts 12 are provided in side portions 301b of the sensor element 301, instead of the external communication part 11 provided in the end portion 101a of the sensor element 101 according to the first preferred embodiment. In this preferred embodiment, a part extending from the external communication parts 12 to the second internal space 40 is also referred to as a gas distribution part 113.

Similarly to the external communication part 11, the external communication parts 12 are spaces within the sensor element 301 provided by hollowing out the spacer layer 5, in which their upper portions is defined by the lower surface of the second solid electrolyte layer 6 or the internal surface 5a of the spacer layer 5, their lower portions is defined by the upper surface of the first solid electrolyte layer 4 or the internal surface 5b of the spacer layer 5, and their side portions are defined by side surfaces 5e and 5f of the spacer layer 5. In more detail, the positions where the external communication parts 12 are formed are adjusted in accordance with the degree of the diffusion resistance suitable for measurement of the nitrogen oxide (NOx) concentration.

A width e of the external communication part 12 in the x-axis direction and a thickness f of the external communication part 12 in the z-axis direction are defined in accordance with the degree of the diffusion resistance to be applied to the measurement gas introduced from an opening 12a into the first internal space 20.

Here, in the external communication part 12, similarly to the external communication part 11, it is preferable that the thickness f is 50% to 100% of the thickness d of the first internal space 20 in the z-axis direction and the width e is 5% to 60% (desirably 10% to 40%) of the width c of the first internal space 20 in the y-axis direction.

In this manner, in the gas sensor 300, the width e and the thickness f of the external communication part 12 are defined within the range mentioned above, thereby suppressing entry of water adhering to the side portion 301b of the sensor element 301 into the first internal space 20.

In the external communication part 12, it is preferable that a distance t1 in the x-axis direction from an end of the first internal space 20 at the element end portion side to the communication parts 12b is equal to or less than 20% of a length t2 of the first internal space 20 in the x-axis direction. The distance t1 exceeding 20% makes it difficult to adjust oxygen partial pressure in the measurement gas within the first internal space 20. The value of t1 may be 0, because it allows the oxygen partial pressure to be adjusted more effectively.

As described above, in the gas sensor 300 according to this preferred embodiment, the external communication parts 12 having the openings 12a formed in the side portions 301b of the sensor element 301 are provided, to thereby suppress entry of water adhering to an end portion 301a of the sensor element 301 due to the capillarity. Moreover, suitably setting the size of the external communication part 12 also suppresses entry of water adhering to the side portion 301b of the sensor element 301 due to the capillarity. This can consequently suppress occurrence of cracking in the sensor element 301 which may otherwise be caused by rapid vaporization of the water in the internal space.

Additionally, in the gas sensor 300 according to this preferred embodiment, the external communication part 12 having the opening 12a formed in the side portion 301b of the sensor element 301 is provided instead of an external communication part having an opening formed in the end portion 301a of the sensor element 301. This improves the strength of a portion near the end portion 301a of the sensor element 301. As a result, occurrence of cracking in the sensor element 301 is suppressed which may otherwise be caused by a thermal stress water adhering to the end portion 301a of the sensor element 301.

Therefore, in the gas sensor 300 according to this preferred embodiment, a deterioration in the measurement accuracy which may be caused by occurrence of cracking in the sensor element 301 can be suitably suppressed. In other words, even if water adheres to the end portion 301a of the sensor element 301 during the operation of the gas sensor 300, the measurement accuracy is stably maintained.

As described above, according to this preferred embodiment, the external communication part 12 having a predetermined size is provided in the side portion 301b of the sensor element 301, to thereby achieve a gas sensor whose measurement accuracy can be stably maintained even if water adheres to the end portion 301a of the sensor element 301 during the operation.

Fourth Preferred Embodiment

In a fourth preferred embodiment, a configuration of a gas distribution part is different from that of the gas sensor 300 according to the third preferred embodiment.

Figure 8A:
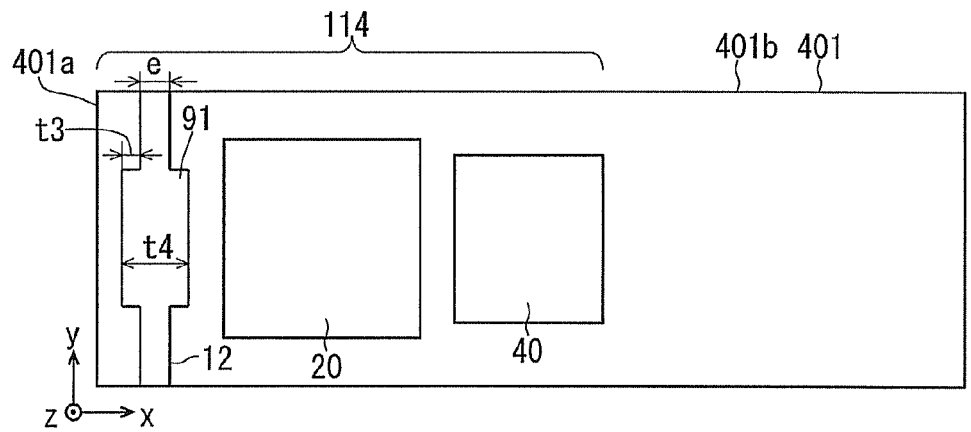
FIGS. 8A, 8B, and 8C are schematic cross-sectional views showing outline cross-sections of the sensor element of the gas sensor according to the fourth preferred embodiment.
Figure 8B:
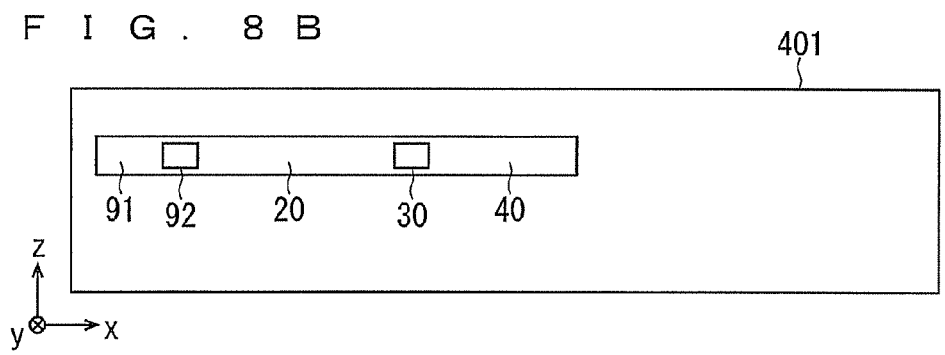
Figure 8C:
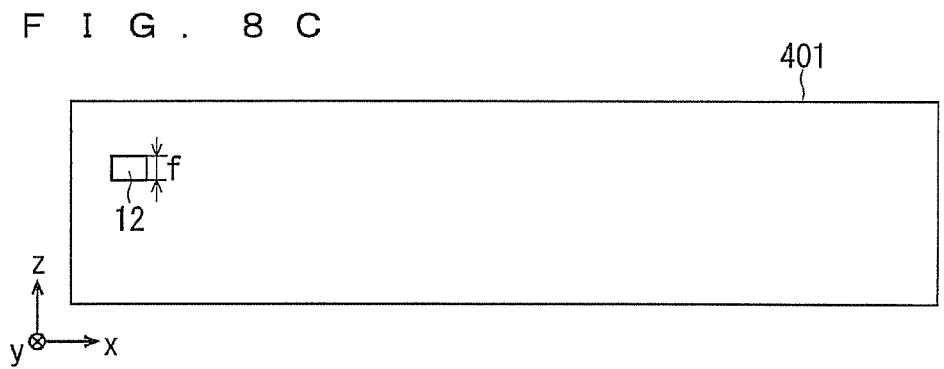

FIG. 7 is an external appearance perspective view showing an outline of an exemplary configuration of a sensor element 401 of a gas sensor 400 according to the fourth preferred embodiment. FIGS. 8A, 8B, and 8C are schematic cross-sectional views showing outline cross-sections of the sensor element 401 as sectioned at different positions shown in FIG. 7, for explaining the structure of a gas distribution part 114. In FIGS. 8A, 8B, and 8C, for simplification, components other than the gas distribution part 114 are omitted. FIG. 8A shows a cross-section as sectioned along the arrow A-A' of FIG. 7. FIG. 8B shows a cross-section as sectioned along the arrow B-B' of FIG. 7. FIG. 8C shows a cross-section as sectioned along the arrow C-C' of FIG. 7. The same components as those of the gas sensor 100 according to the first preferred embodiment or the gas sensor 300 according to the third preferred embodiment are denoted by the same corresponding reference numerals, and descriptions and drawings thereof are omitted.

In the sensor element 401, a buffer space 91 and a third diffusion control part 92 are provided between the external communication parts 12 and the first internal space 20 of the sensor element 301 according to the third preferred embodiment. In this preferred embodiment, a part extending from the external communication parts 12 to the second internal space 40 is also referred to as the gas distribution part 114. In this preferred embodiment, the buffer space 91 is provided such that its width t4 in the x-axis direction can be larger than the width e of the external communication part 12. As a result, a buffering effect similar to that of the second preferred embodiment can be obtained.

In the sensor element 401, the external communication parts 12, the buffer space 91, and the third diffusion control part 92, as a whole, apply a predetermined diffusion resistance suitable for measurement of the nitrogen oxide (NOx) concentration to the measurement gas introduced from the opening 12a to the second internal space 20.

The values of the width e and the thickness f which define the value of the diffusion resistance applied in the external communication parts 12 may be set in consideration of the relationship with the diffusion resistance to be applied in the third diffusion control part 92. In this preferred embodiment, similarly to the third preferred embodiment, it is preferable that the thickness f of the external communication parts 12 is 50% to 100% of the thickness d of the first internal space 20 in the z-axis direction, and the width e of the external communication parts 12 is 5% to 60% (desirably 10% to 40%) of the width c of the first internal space 20 in the y-axis direction. This can suppress occurrence of the capillarity.

In the external communication parts 12, it is preferable that a distance t3 in the x-axis direction from an end of the buffer space 91 at the element end portion side to the communication part 12b is equal to or less than 50% of a length t4 of the buffer space 91 in the x-axis direction. The distance t3 exceeding 50% makes it difficult to cancel a rapid change of the concentration fluctuation in the measurement gas within the buffer space 91.

As described above, according to this preferred embodiment, similarly to the third preferred embodiment, a gas sensor can be achieved in which the measurement accuracy can be stably maintained even if water adheres to the end portion 401a of the sensor element 401 during the operation, and moreover, since the buffer space 91 and the third diffusion control part 92 are provided, a concentration fluctuation in the measurement gas can be suitably suppressed even if the measurement gas is abruptly taken into the sensor element 401 along with a pressure fluctuation in the measurement gas.

<Modification>

Although in the above description, the first diffusion control part 30 and the third diffusion control part 92 are formed as horizontally elongated slits, applications of the present invention are not limited thereto. The first diffusion control part 30 and the third diffusion control part 92 may be formed into other shapes.

Additionally, although in the third preferred embodiment and the fourth preferred embodiment, one external communication part is provided in each of the side portions of the sensor element, applications of the present invention are not limited thereto. Two or more external communication parts may be provided in each of the side portions of the sensor element. Alternatively, the external communication part may be provided in only one of the side portions.

Figure 9A:
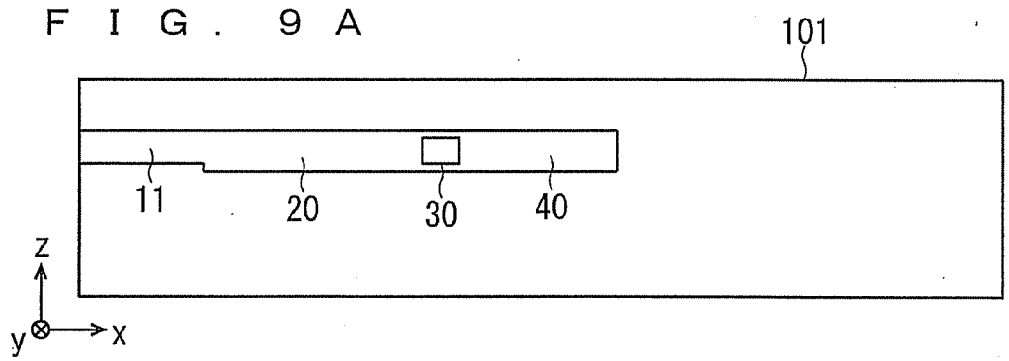
FIGS. 9A, 9B, and 9C are schematic cross-sectional views showing a modification of the gas sensor according to the present invention.
Figure 9B:
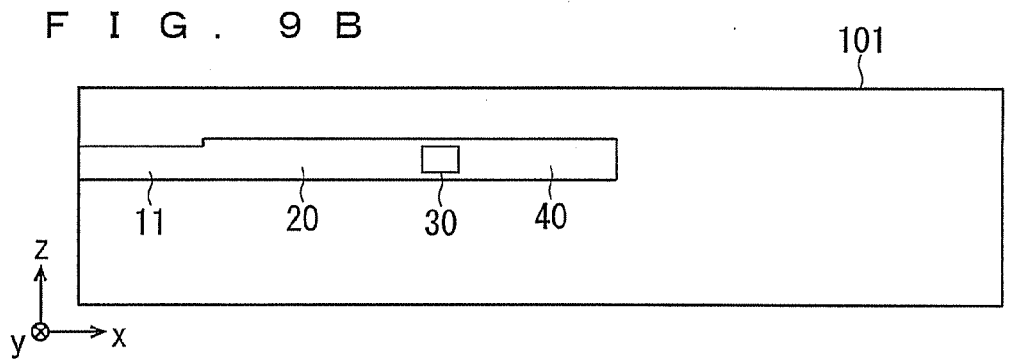
Figure 9C:
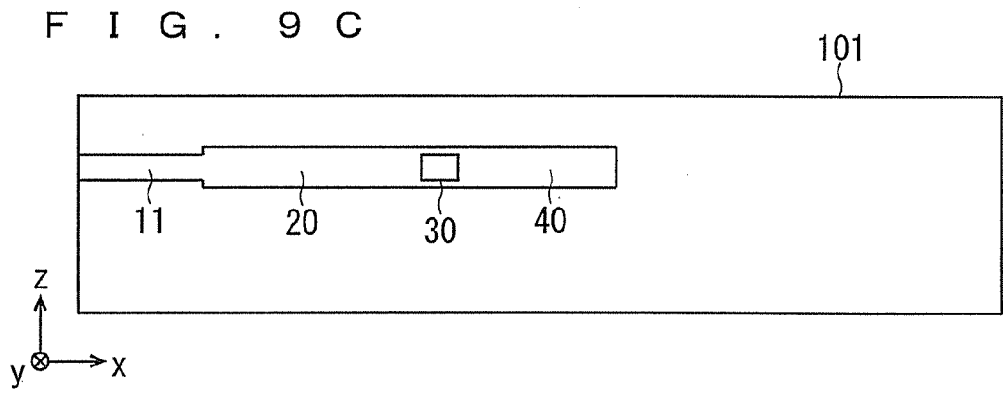

In a case where the thickness of the external communication part is smaller than the thickness of the first internal space, the external communication part may be formed in either upper or lower portion of the spacer layer 5, as shown in FIG. 9A and FIG. 9B, or may be formed substantially in the middle of the spacer layer 5, as shown in FIG. 9C.

EXAMPLES

Example 1

A water drop test was performed on a gas sensor A which is an example of the gas sensor 100 according to the first preferred embodiment, a gas sensor B which is an example of the gas sensor 200 according to the second preferred embodiment, gas sensors C and D which are examples of the gas sensor 300 according to the third preferred embodiment, gas sensors E and F which are examples of the gas sensor 400 according to the fourth preferred embodiment, and a gas sensor G which is a comparative example.

In the gas sensor C, the distance t1 is 0. In the gas sensor D, the distance t1 is 10% of the length t2. In the gas sensor E, the distance t3 is 0. In the gas sensor F, the distance t3 is 10% of the length t4. The gas sensor G is a conventional gas sensor in which slit-shaped external communication part having an opening is provided in an end portion of a sensor element. In the gas sensor G, the width of the external communication part is equal to the hollow-chamber width, and the thickness of the external communication part is 5% of the hollow-chamber thickness.

In the water drop test, in a state where the gas sensor was driven while the sensor element was heated at a predetermined temperature, a water droplet was dropped to or near an end portion of the sensor element, and whether cracking occurred in the sensor element or not was examined. In the test, the amount of dropped water droplet was increased until cracking occurred in the sensor element. At a time point when cracking occurred in the sensor element, the driving of the gas sensor was stopped and the amount of water droplet at this time point was measured. A cracking water droplet amount ratio is a value represented by a ratio of a water droplet amount causing cracking in each of the gas sensors A to F with respect to a water droplet amount causing cracking in the gas sensor G.

Figure 10:
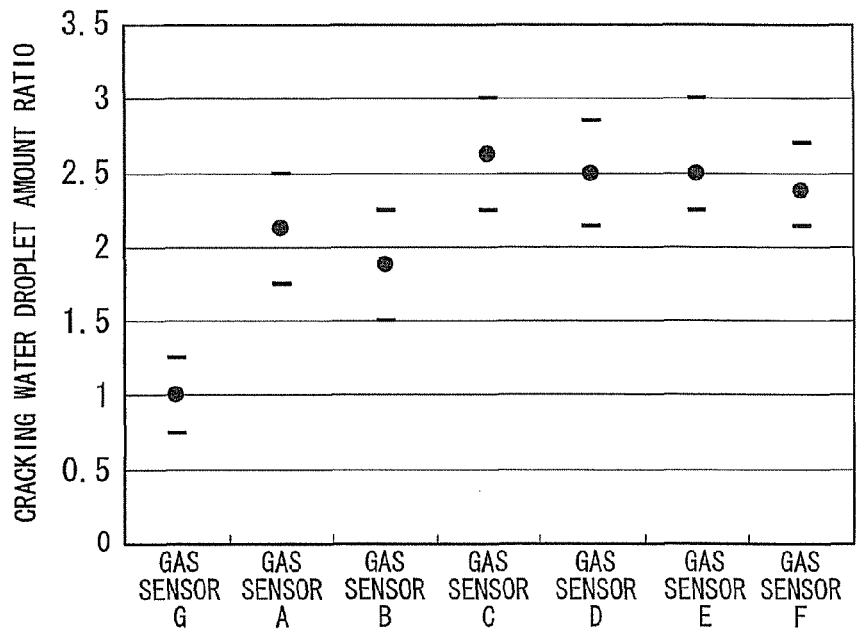
FIG. 10 is a diagram showing the relationship between the fracture strength and the structure of an external communication part.

FIG. 10 shows a result of measurement of a cracking water droplet amount in each of the gas sensors A to F. In the gas sensor A, the width a is 20% of the width c, and the thickness b is 100% of the thickness d. In the gas sensor B, the width a is 10% of the width c, and the thickness b is 100% of the thickness d. In the gas sensor C, the width e is 20% of the width c, and the thickness f is 100% of the thickness d. In the gas sensor D, the width e is 30% of the width c, and the thickness f is 50% of the thickness d. In the gas sensor E, the width e is 20% of the width c, and the thickness f is 100% of the thickness d. In the gas sensor F, the width e is 15% of the width c, and the thickness f is 80% of the thickness d. For each of the gas sensors A to G, the number of measured gas sensors was five.

In FIG. 10, the circles indicate average values of measurement values, and the lines above and below the circles indicate the maximum values and the minimum values of the measurement values. As shown in FIG. 10, it is observed that the cracking water droplet amounts of the gas sensors A to F were larger than that of the gas sensor G. This result means that the gas sensors A to F have fracture strengths larger than that of the gas sensor G.

Example 2

In this example, for examining the relationship between the size of the external communication part and the fracture strength, a plurality of gas sensors were prepared for each of the preferred embodiments, the plurality of gas sensors being different from one another in the ratio of the size of the external communication part to the size of the hollow chamber. Then, the same water drop test as that of the example 1 was performed.

Figure 11:
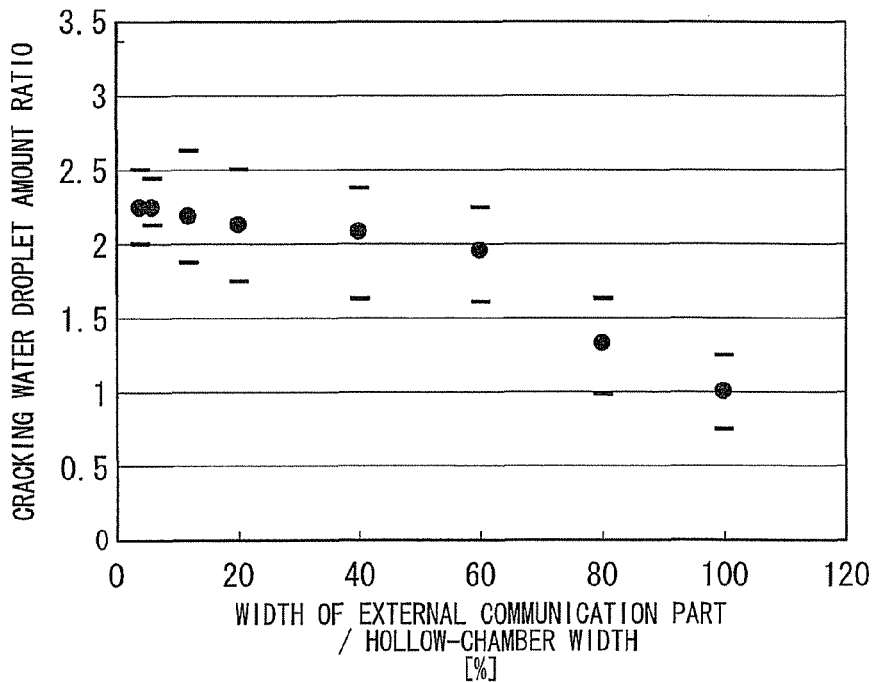
FIG. 11 is a diagram showing the relationship between the fracture strength and the width of an external communication part of a gas sensor according to an example equivalent to the first preferred embodiment.
Figure 12:
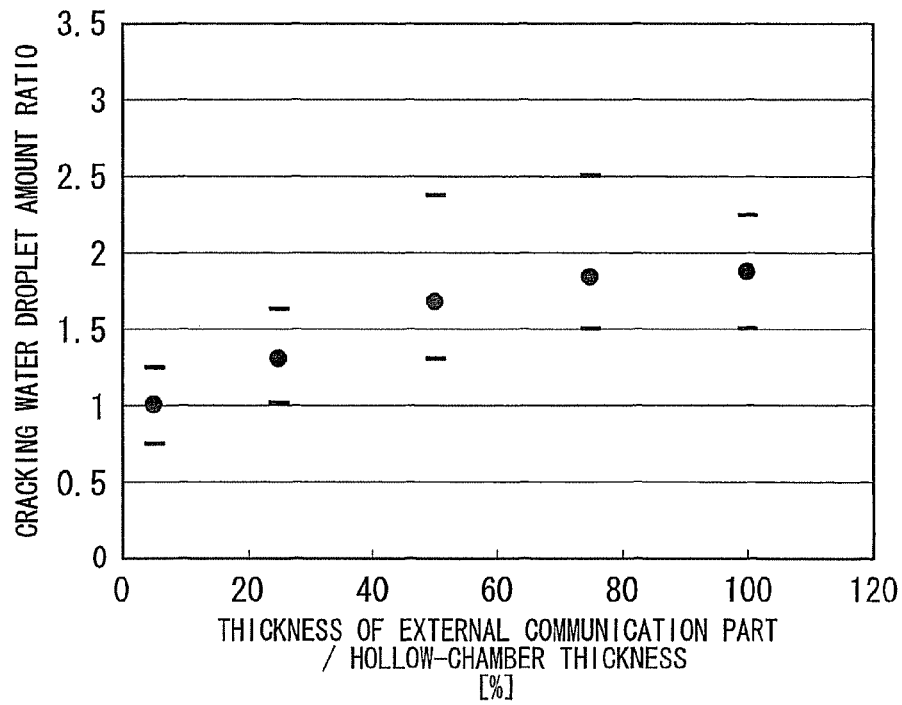
FIG. 12 is a diagram showing the relationship between the fracture strength and the thickness of an external communication part of a gas sensor according to an example equivalent to the second preferred embodiment.
Figure 13:
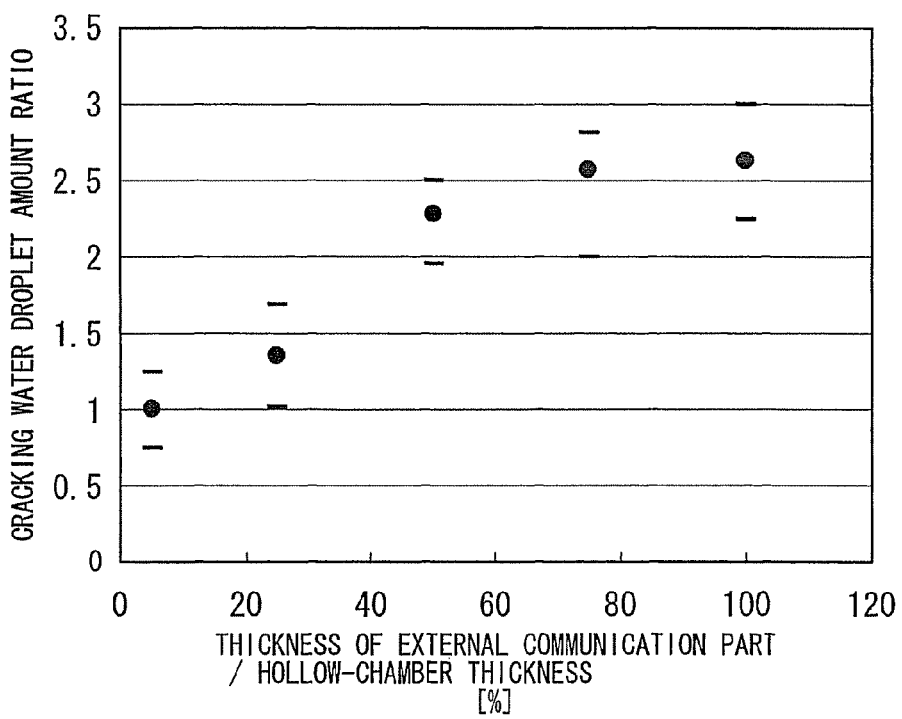
FIG. 13 is a diagram showing the relationship between the fracture strength and the thickness of an external communication part of a gas sensor according to an example equivalent to the third preferred embodiment.
Figure 14:
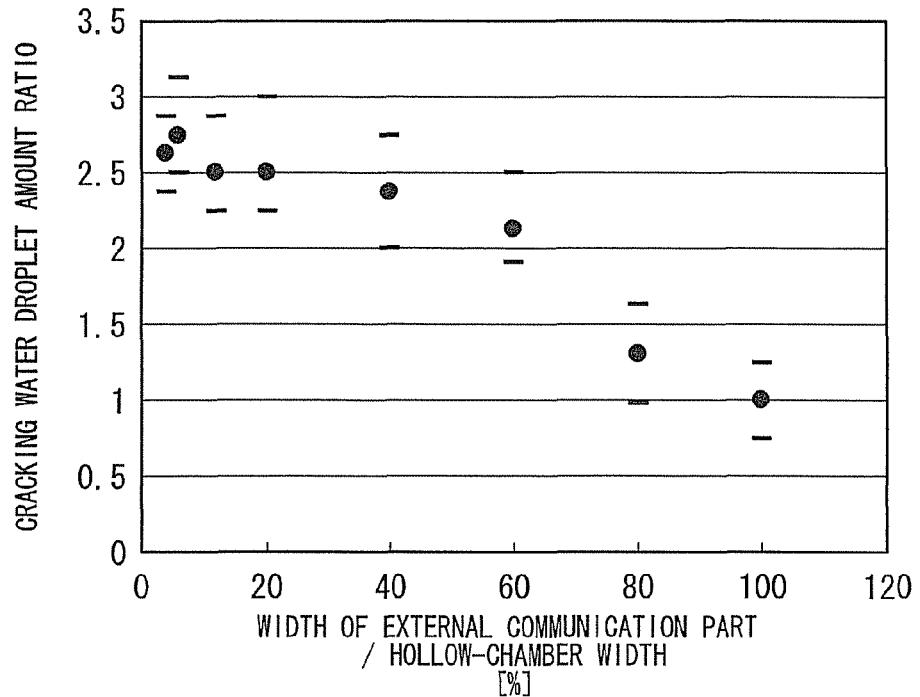
FIG. 14 is a diagram showing the relationship between the fracture strength and the width of an external communication part of a gas sensor according to an example equivalent to the fourth preferred embodiment.

FIG. 11 shows a result of measurement of the cracking water droplet amount of each of the eight types of gas sensors corresponding to the first preferred embodiment. The eight types of gas sensors are different from one another in the width a of the external communication part 11. FIG. 12 shows a result of measurement of the cracking water droplet amount of each of the five types of gas sensors corresponding to the second preferred embodiment. The five types of gas sensors are different from one another in the thickness b of the external communication part 12. FIG. 13 shows a result of measurement of the cracking water droplet amount of each of five types of gas sensors corresponding to the third preferred embodiment. The five types of gas sensors are different from one another in the thickness for the external communication part 12. FIG. 14 shows a result of measurement of the cracking water droplet amount of each of eight types of gas sensors corresponding to the fourth preferred embodiment. The eight types of gas sensors are different from one another in the width e of the external communication part 12. For each type of the gas sensor, the number of measured gas sensors was five. Here, it is to be noted that, the cases where the ratio of the width of the external communication part to the hollow-chamber width was 100% in FIGS. 11 and 14, and the cases where the ratio of the thickness of the external communication part to the hollow-chamber thickness was 5% in FIGS. 12 and 13 were results of measurement with respect to the gas sensor G which is a comparative example.

The circles in FIGS. 11 to 14 indicate average values of measurement values, and the lines above and below the circles indicate the maximum values and the minimum values of the measurement values. As shown in FIGS. 11 to 14, it is observed that the cracking water droplet amount of any of the gas sensors according to this example was larger than that of the gas sensor G according to the comparative example, irrespective of the width or the thickness of the external communication part. This result means that any of the gas sensors according to this example had a larger fracture strength than that of the gas sensor G according to the comparative example, irrespective of the width or the thickness of the external communication part. Particularly, in a case where the ratio of the width of the external communication part to the hollow-chamber width was 5% or more and 60% or less, and a case where the ratio of the thickness of the external communication part to the hollow-chamber thickness was 50% or more and 100% or less, the cracking water droplet amount was twice or more of that of the gas sensor according to the comparative example. This indicates that providing the external communication part so as to satisfy these sizes can achieve a gas sensor having a doubled fracture strength as compared with the conventional gas sensor.

From the results of the examples 1 and 2, it is confirmed that providing the external communication part whose size is set so as to satisfy the above-mentioned requirements is effective in improving the fracture strength. In both of the examples 1 and 2, it is confirmed that providing the external communication part having an opening in a side portion of the sensor element (corresponding to the third and fourth preferred embodiments) is more effective in improving the fracture strength. This result means that providing the above-described external communication part is effective in suppressing a deterioration in the measurement accuracy which may otherwise be caused by occurrence of cracking in the sensor element.

Example 3

In this example, the respective gas sensors of the example 1 were examined for the responsiveness. In a test of the responsiveness, in a case where an air-fuel ratio (a oxygen concentration in a measurement gas) of a measurement gas was changed from $\lambda=0.9$ to $\lambda=1.1$, a sensor output (Ip2) obtained at a time when the inside of the sensor element was substantially fully replaced with the measurement gas having an air-fuel ratio of $\lambda=0.9$ was defined as 0%, and the sensor output (Ip2) obtained at a time when the inside of the sensor element was substantially fully replaced with a measurement gas having an air-fuel ratio of $\lambda=1.1$ was defined as 100%. Under this condition, a time (response time) from the time point when the sensor output (Ip2) corresponding to 33% was detected to the time point when the sensor output (Ip2) corresponding to 66% was detected was measured three times for each of the gas sensors.

Figure 15:
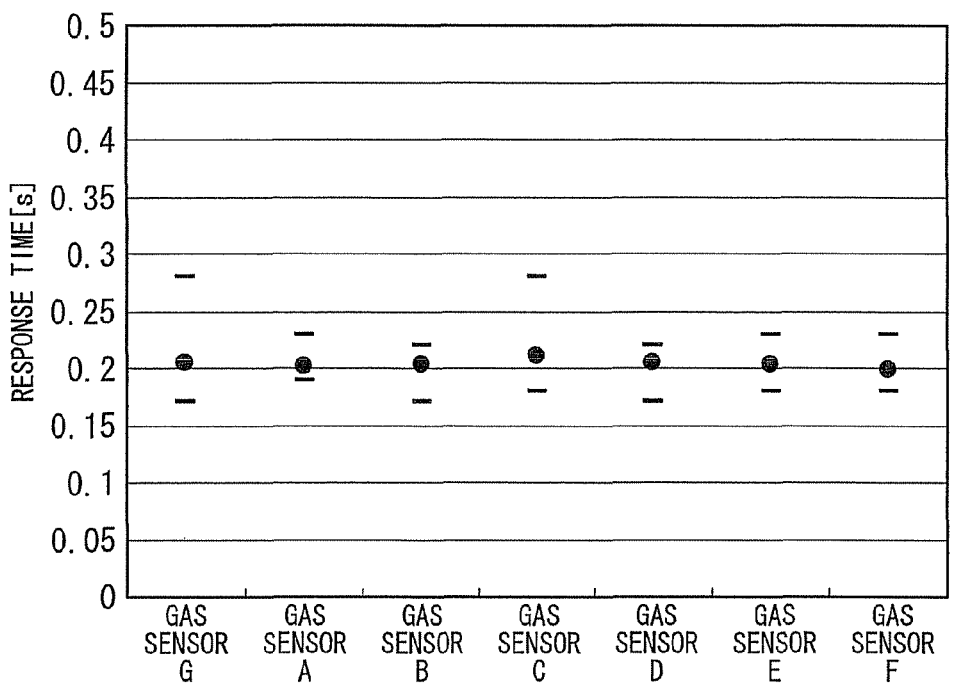
FIG. 15 is a diagram showing a result of measurement of a response time for gas sensors according to examples and a comparative example.

FIG. 15 shows a result of measurement of the response time of each of the gas sensors A to G. In each of the gas sensors A to F, the relationship between the width of the external communication part and the width c, and the relationship between the thickness of the external communication part and the thickness d were the same as those of the gas sensors used in the water drop test shown in FIG. 10.

In FIG. 15, the circles indicate average values of the measurement values, and the lines above and below the circles indicate the maximum values and the minimum values of the measurement values. As shown in FIG. 15, no significant difference was observed between the response times of the gas sensors A to F and the resonse time of the gas sensor G.

The above-described results reveal that responsiveness equivalent to the responsiveness of the conventional gas sensor can be obtained also by the gas sensors A to F provided with the external communication part that satisfies the above-mentioned requirements.

What is claimed is:

1. A gas sensor for detecting a predetermined gas component in a measurement gas, said gas sensor comprising:
a sensor element constituted by an oxygen-ion conductive solid electrolyte as a main component and having an upper portion, a lower portion, opposing end portions and opposing side portions;
an external communication part having an opening opened to the outside, and introducing the measurement gas from the outside under a predetermined diffusion resistance;
an internal space communicating with said external communication part;
a first electrode formed on a surface of said internal space;
a second electrode formed in a space different from said internal space;
a pumping cell operable to pump out oxygen existing in said internal space when a predetermined voltage is applied between said first electrode and said second electrode; and
a buffer space provided between said external communication part and said internal space,
wherein said external communication part is a space having a constant width along a longitudinal direction of the sensor element,
wherein the thickness of said external communication part is 50% or more and 100% or less of the thickness of said internal space, and the width of said external communication part is 5% or more and 60% or less of the width of said internal space,
wherein a width of the buffer space is larger than a width of said external communication part, and
wherein the buffer space is directly connected to said external communication part.

2. The gas sensor according to claim 1, wherein said external communication part has said opening formed in at least one side portion of the opposed side portions of said sensor element.

3. The gas sensor according to claim 1, wherein said external communication part has said opening formed in one end portion of the opposing end portions of said sensor element.

4. The gas sensor according to claim 1, wherein said internal space further comprises a first internal space and a second internal space, said first internal space being in communication with said external communication part and said second internal space; and
said pumping cell further comprises a main pumping cell and an auxiliary pumping cell,
wherein
said first internal space is in communication with said external communication part under a predetermined diffusion resistance,
said second internal space is in communication with said first internal space under a predetermined diffusion resistance,
said main pumping cell has said first electrode provided in said first internal space, and
said auxiliary pumping cell has a third electrode provided in said second internal space.

5. The gas sensor according to claim 4, wherein said sensor element further comprises:
a fourth electrode formed on a surface of said second internal space;
a measuring cell including said fourth electrode and said second electrode; and
a porous diffusion layer formed on said fourth electrode and applying a predetermined diffusion resistance to said measurement gas,
said main pumping cell is operable to pump out oxygen existing in said first internal space when a predetermined voltage is applied between said first electrode provided in said first internal space and said second electrode,
said auxiliary pumping cell is operable to pump out oxygen existing in said second internal space when a predetermined voltage is applied between said third electrode provided in said second internal space and said second electrode,
said fourth electrode reduces an oxide gas component in said predetermined gas component to which said predetermined diffusion resistance has been applied by said porous diffusion layer,
said measuring cell is operable to measure an electromotive force between said fourth electrode and said second electrode to determine a nitrogen oxide concentration in the measurement gas using a pump current between said fourth electrode and said second electrode.

* * * * *